United States Patent
Tsai et al.

(10) Patent No.: US 10,511,820 B2
(45) Date of Patent: Dec. 17, 2019

(54) PSEUDO HANDE IMAGE PRODUCING METHOD AND OPTICAL SYSTEM USING SAME

(71) Applicant: AcuSolutions Inc., Apia (WS)

(72) Inventors: Chien-Chung Tsai, Taipei (TW); Kuang-Yu Hsu, Taipei (TW)

(73) Assignee: ACUSOLUTIONS INC., Apia (WS)

( * ) Notice: Subject to any disclaimer, the term of this patent is extended or adjusted under 35 U.S.C. 154(b) by 76 days.

(21) Appl. No.: 15/864,323

(22) Filed: Jan. 8, 2018

(65) Prior Publication Data
US 2019/0028687 A1 Jan. 24, 2019

(30) Foreign Application Priority Data
Jul. 19, 2017 (TW) .............................. 106124193 A (51) Int. Cl.
| G06K 9/00 | (2006.01) |
| H04N 9/43 | (2006.01) |
| G06T 5/50 | (2006.01) |
| G06T 7/00 | (2017.01) |
| G01N 21/64 | (2006.01) |
| G06T 11/00 | (2006.01) |

(52) U.S. Cl.
CPC .............. H04N 9/43 (2013.01); G01N 21/64 (2013.01); G06T 5/50 (2013.01); G06T 7/0014 (2013.01); G06T 11/001 (2013.01); G01N 21/6458 (2013.01); G06T 2207/10024 (2013.01); G06T 2207/10056 (2013.01); G06T 2207/10064 (2013.01); G06T 2207/20221 (2013.01); G06T 2207/30004 (2013.01); G06T 2207/30024 (2013.01)

(58) Field of Classification Search
CPC .. G01N 21/64; G01N 21/6458; G06T 11/001; G06T 2207/10024; G06T 2207/10056; G06T 2207/10064; G06T 2207/20221; G06T 2207/30004; G06T 2207/30024; G06T 5/50; G06T 7/0014; H04N 9/43
See application file for complete search history.

(56) References Cited

U.S. PATENT DOCUMENTS

| 8,269,827 B2 | 9/2012 | Can et al. |
| 2010/0150423 A1* | 6/2010 | Hong .................. G06K 9/0014 382/133 |

(Continued)

Primary Examiner — Xin Jia
(74) Attorney, Agent, or Firm — Guice Patents PLLC (57) ABSTRACT

A pseudo H&E image producing method, including: inputting a grayscale interference image or a grayscale reflected image of a pathological sample to a first memory block of an information processing apparatus, and inputting a grayscale fluorescence image of the pathological sample to a second memory block of the information processing apparatus; using the information processing apparatus to perform a first color transform operation on the grayscale interference image or the grayscale reflected image to generate a first RGB image, and using the information processing apparatus to perform a second color transform operation on the grayscale fluorescence image to generate a second RGB image; and using the information processing apparatus to perform an image fusion operation and an intensity reversal operation on the first RGB image and the second RGB image to generate a pseudo H&E image. The present invention also discloses an optical system using the method.

9 Claims, 5 Drawing Sheets

(56) References Cited

U.S. PATENT DOCUMENTS

| | | | | |
|---|---|---|---|---|
| 2014/0154793 A1* | 6/2014 | Naito | ............... | G01N 15/1429 |
| | | | | 435/288.7 |
| 2014/0161369 A1* | 6/2014 | Ishihara | ............... | A61B 1/043 |
| | | | | 382/274 |
| 2016/0003716 A1* | 1/2016 | Torres | ............ | G01N 1/30 |
| | | | | 435/40.52 |
| 2018/0315215 A1* | 11/2018 | Mroz | ................ | H04N 19/196 |

* cited by examiner

PSEUDO HANDE IMAGE PRODUCING METHOD AND OPTICAL SYSTEM USING SAME

BACKGROUND OF THE INVENTION

Field of the Invention

The present invention relates to a hybrid image generating method of an optical system, especially to a pseudo H&E image producing method and an optical system using the method.

Description of the Related Art

In conventional tumor surgery, it takes a lot of time for a pathologist to examine a frozen section to determine if a tumor is cleanly removed. However, during the process of preparing a frozen section of a pathological sample, if the pathological sample contains much water, a formed crystal ice structure will cause a damage to the tissue structure of the pathological sample; and if the pathological sample contains much fat, the fat will remain unfrozen at temperatures around −20° C. where the other tissues are already frozen, and is therefore easy to slip off from the frozen section to cause an artifact to the frozen section. Besides, frozen cells are generally not easily stained. Due to the facts disclosed above, the artifact, which does not exist in fresh tissues of the pathological sample, will be present in the image of the frozen section of the pathological sample. To cope with this problem, optical inspection instrument has been adopted to provide a real time pseudo H&E image of a sliced sample for medical personnel to inspect, and the pseudo H&E image is derived by a non-destructive optical sectioning scheme without the need of slicing a frozen sample.

General optical sectioning method performs a linear combination of a plurality of grayscale images of a pathological sample to generate a black-background RGB image, so that when the black-background RGB image is viewed by the eyes of a person, the person will sense as if a color image is present in a dark space. The plurality of grayscale images are generated by performing a plurality of different image producing methods on the pathological sample, the color of each pixel of the color image is determined by a combination of three primary colors (red, green, blue), and the intensity values of the three primary colors of each pixel are determined by three linear combinations of corresponding pixels of the plurality of grayscale images. Besides, conventional image producing scheme, such as satellite image scheme, X-ray image scheme, or electronic microscopic image scheme, can only present image of grayscale format due to single image intensity distribution. If the image can be displayed in color format, not only readability and distinguishability of the image can be improved, but also more information can be provided with the image.

Besides, as far as color contrast is concerned, red and green have the highest degree of contrast. However, when a person has viewed a lot of red-and-green images with black background or has viewed a red-and-green image with black background for a long time, his/her eyes will feel uncomfortable and fatigued. As a result, the format of red-and-green image with black background is not suitable for the image of a pathological sample, because a pathologist may have to inspect a lot of images of pathological samples during a work day. At present time, pathological image is generally generated by firstly staining a pathological sample section (paraffin section or frozen section) with Hematoxylin and Eosin, and then executing an image producing procedure to generate a tender white-background image, where the Hematoxylin and Eosin will paint nuclei and cytoplasm with blue-purple color and pink color respectively, and as different parts in the cytoplasm respond differently in sticking to the Eosin and by which different shades of pink color will be generated correspondingly, the H&E staining color image can therefore provide more detailed pathological information. Therefore, if the commonly used black-background RGB image can be replaced with white-background RGB image like H&E image, it will be very helpful to a pathologist who needs to inspect a lot amount of images. However, as traditional pathological image producing method not only has an artifact issue, but also requires a long time, it is therefore not suitable for providing a timely pathological image needed in a surgery.

U.S. Pat. No. 8,269,827B2 "System and methods for mapping fluorescent images into a bright field color space" discloses a method of using fluorescent images to generate a pseudo H&E image, including: deriving two or more fluorescent images of a specified area of a pathological sample; and using mapping parameters to transfer the fluorescent images into a bright field color space to generate a bright-field image.

However, as the U.S. Pat. No. 8,269,827B2 uses fluorescent images to generate a pseudo H&E image, it has disadvantages as follows: (1) the color contrast of the pseudo H&E image is not good enough due to a fact that the internal structure of a pathological sample cannot be uniformly stained with a fluorescent agent; (2) the fluorescent agents used for generating the fluorescent images will cause damage to the pathological sample; and (3) it takes a lot of time to stain the fluorescent agents onto the pathological sample. Therefore, there is a need of a novel method for producing a pseudo H&E image in the field.

SUMMARY OF THE INVENTION

One objective of the present invention is to disclose a pseudo H&E image producing method, which generates a pseudo H&E image of a pathological sample without the need of performing a physically slicing procedure on the pathological sample, where the pseudo H&E image is a white-background RGB image having excellent color contrast and is generated by letting an interference image (or a reflected image) and a fluorescent image of the pathological sample undergo a color transform procedure, an image fusion procedure and an intensity reversal procedure.

Another objective of the present invention is to disclose a pseudo H&E image producing method, which is capable of using less fluorescent agent to minimize the damage on a pathological sample caused by the fluorescent agent compared to the prior art method of using multiple fluorescent images.

Another objective of the present invention is to disclose a pseudo H&E image producing method, which, in comparison with the prior art method of using multiple fluorescent images, is capable of using less fluorescent agent to shorten a staining time and thereby speed up the completion of a pseudo H&E image.

Still another objective of the present invention is to disclose a pseudo H&E image producing method, in which, in comparison with conventional H&E image, the pseudo H&E image thereof is capable of providing more detailed image information of the cytoplasm and nuclei, thereby enhancing the distinguishability between normal tissues and abnormal tissues.

To attain the foregoing objectives, a pseudo H&E image producing method is proposed, including steps of: inputting a grayscale interference image or a grayscale reflected image of a pathological sample to a first memory block of an information processing apparatus, the grayscale interference image or the grayscale reflected image having a first image resolution, and inputting a grayscale fluorescence image of the pathological sample to a second memory block of the information processing apparatus, the grayscale fluorescence image having a second image resolution, and the first image resolution being same with or different from the second image resolution;

using the information processing apparatus to perform a first color transform operation on the grayscale interference image or the grayscale reflected image to generate a first RGB image, and using the information processing apparatus to perform a second color transform operation on the grayscale fluorescence image to generate a second RGB image;

using the information processing apparatus to perform an image fusion operation and an intensity reversal operation on the first RGB image and the second RGB image to generate a pseudo H&E image; and outputting the pseudo H&E image to a display unit.

In one embodiment, the grayscale interference image or the grayscale reflected image represents a cytoplasm image.

In one embodiment, the grayscale fluorescent image represents a nuclei image.

In one embodiment, the grayscale interference image is generated by an optical interference microscopy scheme, which uses interference between a light beam and a reflected light beam to generate an image of the pathological sample.

In one embodiment, the grayscale reflected image is generated by a reflectance confocal microscopy scheme, which uses a directly reflected light beam to generate an image of the pathological sample.

In one embodiment, the first color transform operation sets both red pixel intensity and blue pixel intensity of the first RGB image to 0, and sets green pixel intensity of the first RGB image equal to a product of pixel grayscale of the grayscale reflected image or the grayscale interference image and a weighting value, the weighting value ranging between 0.5 and 1.

In one embodiment, the second color transform operation sets green pixel intensity of the second RGB image to $2^{8m}-1$, m being a positive integer, sets blue pixel intensity of the second RGB image to 0, and sets red pixel intensity of the second RGB image equal to a product of pixel gray scale of the grayscale fluorescent image and a weighting value, the weighting value ranging between 0.5 and 1.

In one embodiment, the first RGB image is a black-background dark green image; the second RGB image is a black-background yellow-green image; and the pseudo H&E image is a white-background pink-and-blue-violet image.

In one embodiment, both the first RGB image and the second RGB image use n binary bits to represent red pixel intensity, green pixel intensity, and blue pixel intensity, the n being a positive integer and a multiple of 8.

To attain the foregoing objective, the present invention further proposes an optical system, which utilizes the pseudo H&E image producing method.

To make it easier for our examiner to understand the objective of the invention, its structure, innovative features, and performance, we use preferred embodiments together with the accompanying drawings for the detailed description of the invention.

BRIEF DESCRIPTION OF THE DRAWINGS

FIG. 2c illustrates an RGB interference image derived by performing a first color transform operation on the grayscale interference image of FIG. 2a.

DETAILED DESCRIPTION OF THE PREFERRED EMBODIMENTS

Figure 1:
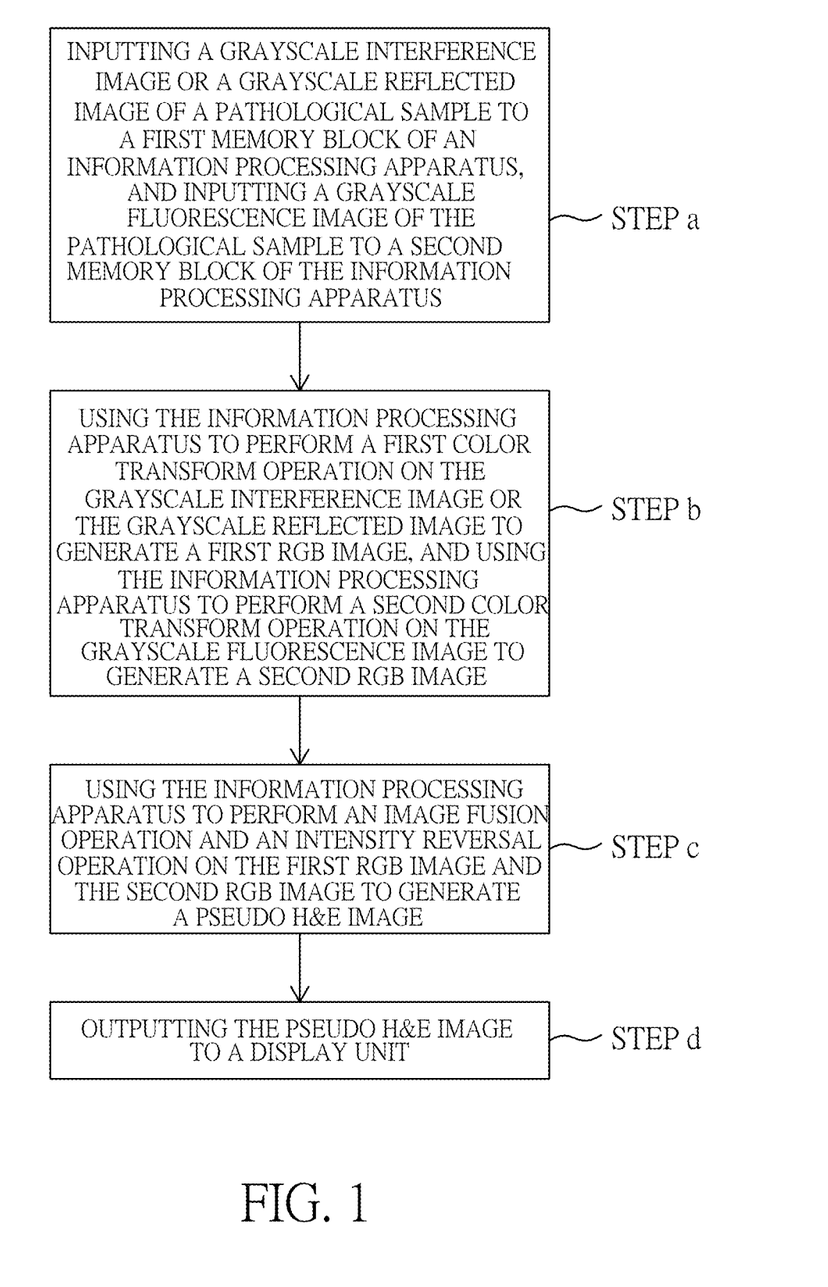
FIG. 1 illustrates a flow chart of pseudo H&E image producing method according to a preferred embodiment of the present invention.

Please refer to FIG. 1, which illustrates a flow chart of pseudo H&E image producing method according to a preferred embodiment of the present invention.

As illustrated in FIG. 1, the pseudo H&E image producing method of the present invention includes the steps of:

inputting a grayscale interference image or a grayscale reflected image of a pathological sample to a first memory block of an information processing apparatus, and inputting a grayscale fluorescence image of the pathological sample to a second memory block of the information processing apparatus (step a); using the information processing apparatus to perform a first color transform operation on the grayscale interference image or the grayscale reflected image to generate a first RGB image, and using the information processing apparatus to perform a second color transform operation on the grayscale fluorescence image to generate a second RGB image (step b); using the information processing apparatus to perform an image fusion operation and an intensity reversal operation on the first RGB image and the second RGB image to generate a pseudo H&E image (step c); and outputting the pseudo H&E image to a display unit (step d). In step a, the grayscale interference image or the grayscale reflected image has a first image resolution, the grayscale fluorescence image has a second image resolution, and the first image resolution can be same with or different from the second image resolution.

The principle of the present invention will be further elaborated below:

The image sources of the pseudo H&E image producing method of the present invention include a grayscale interference image or a grayscale reflected image, and a grayscale fluorescence image, where the grayscale interference image or the grayscale reflected image represents a morphology image of cytoplasm (exterior to nuclei) of a pathological sample, and the grayscale fluorescence image represents an image of nuclei structure.

The grayscale interference image of the pseudo H&E image producing method of the present invention is generated by an OIM (optical interference microscopy) scheme (not shown in the figure), which uses interference between a light beam and a reflected light beam to generate an image of the pathological sample. The optical interference microscopy is known to be able to provide higher space resolution than supersonic method, and it is also known that different tissues of the pathological sample respond differently in light reflection, so the different tissues can be effectively differentiated in an image formed through an optical interference procedure. As the optical interference microscopy scheme is a prior art scheme, it will not be addressed further.

The grayscale reflected image of the pseudo H&E image producing method of the present invention is generated by a RCM (reflectance confocal microscopy) scheme (not shown in the figure), which uses a directly reflected light beam to generate an image of the pathological sample. The reflectance confocal microscopy uses a laser light source to replace a mercury lamp used in a conventional fluorescent microscope, and uses scan mirrors to receive a series of reflected signals in a point-by-point manner to form a two dimensional array image. As the reflectance confocal microscopy scheme is a prior art scheme, it will not be addressed further. Besides, the fluorescent light of the grayscale fluorescent image of the pseudo H&E image producing method of the present invention is a cold light generated by an energy transformation, which transmits a long-wavelength light after absorbing a short-wavelength light. Sensing technology making use of fluorescent response offers great convenience for modern biotechnology, and fluorescent agent is often used as biomarker for indicating cells' state in an imaging process, which uses a short wavelength light beam to illuminate a pathological sample stained with a fluorescent agent, and a fluorescent light will emit thereby to be sensed by a photo sensing device (not shown in the figure). As the fluorescence imaging scheme is a prior art scheme, it will not be addressed further.

Besides, the image of cytoplasm and the image of nuclei generated by the optical sectioning scheme of the present invention are corresponding to an Eosin-absorption-like transmission image and a Hematoxylin-absorption-like transmission image, so the Eosin-absorption-like transmission image and the Hematoxylin-absorption-like transmission image can be combined to form a pseudo H&E image to represent the pattern of a pathological sample. In generating a fluorescent image to represent nuclei, a dye having good membrane permeability is generally adopted to penetrate the surface of the cells to a depth of 100-200 micrometers in a short time, so as to achieve an objective of fast examination. As the fluorescence staining scheme is a prior art scheme, it will not be addressed further.

Figure 2A:
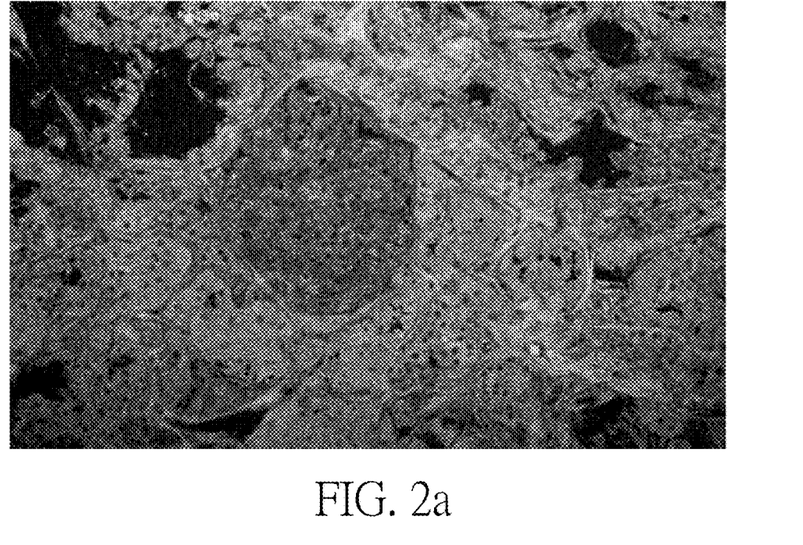
FIG. 2a illustrates a grayscale interference image of a pathological sample according to a preferred embodiment of the present invention.
Figure 2B:
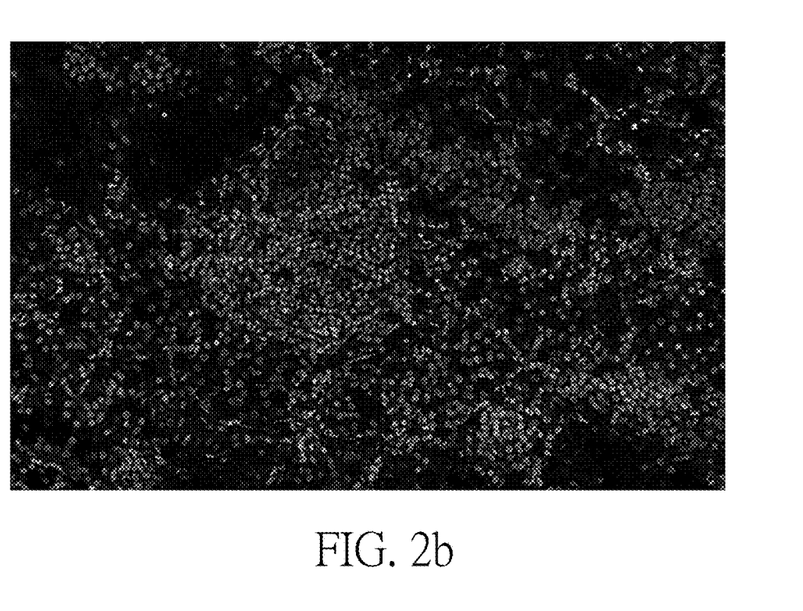
FIG. 2b illustrates a grayscale fluorescent image of a pathological sample according to a preferred embodiment of the present invention.
Figure 2C:
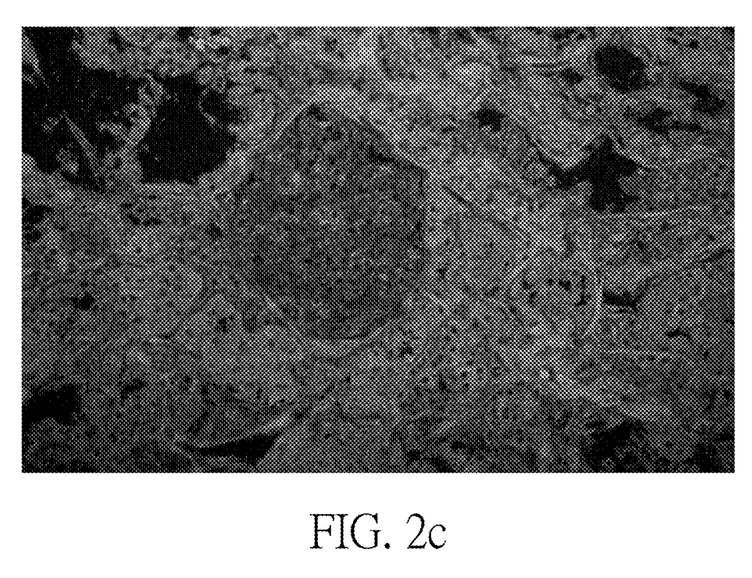
Figure 2D:
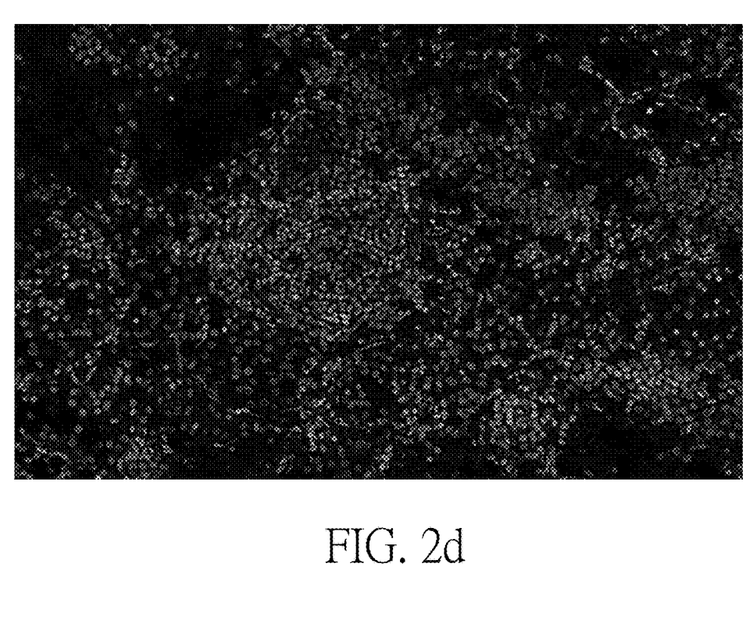
FIG. 2d illustrates an RGB fluorescent image derived by performing a second color transform operation on the grayscale fluorescent image of FIG. 2b.
Figure 2E:
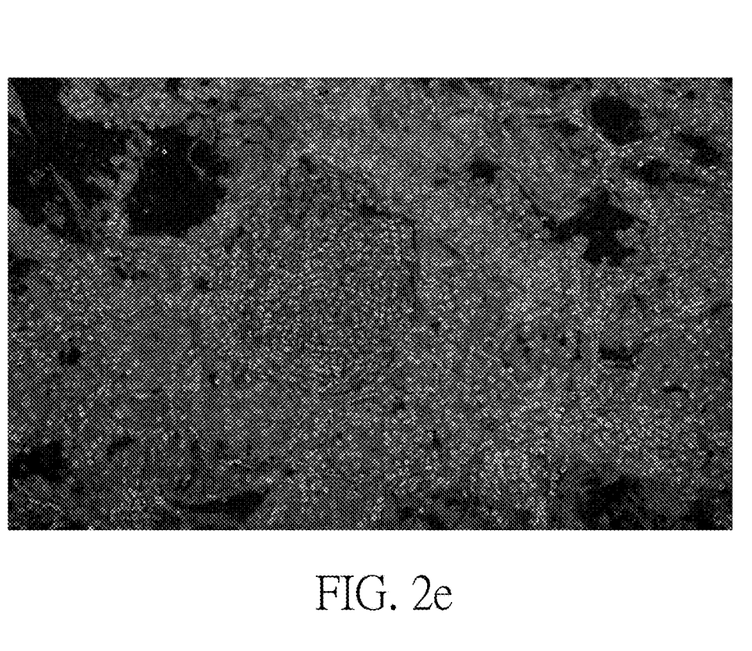
FIG. 2e illustrates an image derived by performing an image fusion operation on the RGB interference image of FIG. 2c and the RGB fluorescent image of FIG. 2d.
Figure 2F:
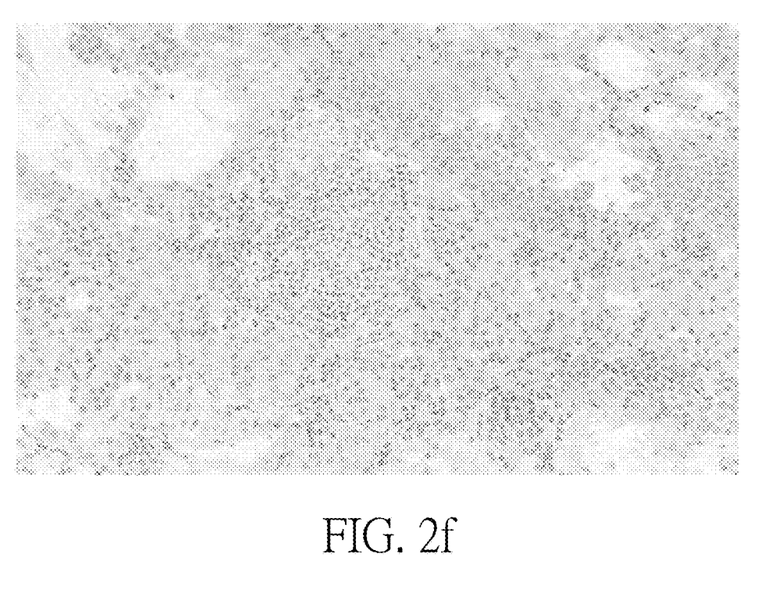
FIG. 2f illustrates a pseudo H&E image derived by performing an intensity reversal operation on the image of FIG. 2e.

Please refer to FIGS. 2a-2f, in which, FIG. 2a illustrates a grayscale interference image of a pathological sample according to a preferred embodiment of the present invention; FIG. 2b illustrates a grayscale fluorescent image of a pathological sample according to a preferred embodiment of the present invention; FIG. 2c illustrates an RGB interference image derived by performing a first color transform operation on the grayscale interference image of FIG. 2a; FIG. 2d illustrates an RGB fluorescent image derived by performing a second color transform operation on the grayscale fluorescent image of FIG. 2b; FIG. 2e illustrates an image derived by performing an image fusion operation on the RGB interference image of FIG. 2c and the RGB fluorescent image of FIG. 2d; and FIG. 2f illustrates a pseudo H&E image derived by performing an intensity reversal operation on the image of FIG. 2e.

The grayscale interference image of FIG. 2a is a black-background image having a first image resolution, and will be stored in a first memory block (not shown in the figure) of an information processing apparatus (not shown in the figure).

The grayscale fluorescent image of FIG. 2b is a black-background image having a second image resolution, and will be stored in a second memory block (not shown in the figure) of the information processing apparatus (not shown in the figure). The first image resolution can be same with or different from the second image resolution.

The first RGB image of FIG. 2c is a black-background dark green image derived by using the information processing apparatus (not shown in the figure) to perform the first color transform operation, where the first color transform operation sets both red pixel intensity and blue pixel intensity of the first RGB image to 0, and makes green pixel intensity of the first RGB image equal to a product of pixel grayscale of the grayscale reflected image or the grayscale interference image and a weighting value, the weighting value ranging between 0.5 and 1.

The second RGB image of FIG. 2d is a black-background yellow-green image derived by using the information processing apparatus (not shown in the figure) to perform the second color transform operation, where the second color transform operation sets green pixel intensity of the second RGB image to $2^{8m}-1$, m being a positive integer, sets blue pixel intensity of the second RGB image to 0, and makes red pixel intensity of the second RGB image equal to a product of pixel grayscale of the grayscale fluorescent image and a weighting value, the weighting value ranging between 0.5 and 1.

FIG. 2e illustrates a black-background image derived by using the information processing apparatus (not shown in the figure) to perform an image fusion operation on the first RGB image (FIG. 2c) and the second RGB image (FIG. 2d).

FIG. 2f illustrates a pseudo H&E image, which is a white-background pink-and-blue-violet image generated by using the information processing apparatus (not shown in the figure) to perform an intensity reversal operation on the black-background image of FIG. 2e.

Besides, both the first RGB image and the second RGB image use n binary bits to represent red pixel intensity, green pixel intensity, and blue pixel intensity, the n being a positive integer and a multiple of 8.

Besides, the grayscale interference image of FIG. 2a can be replaced with a grayscale reflected image, and the grayscale reflected image can be processed with same procedures as the grayscale interference image.

In addition, the present invention also discloses an optical system using the pseudo H&E image producing method.

Figure 3:
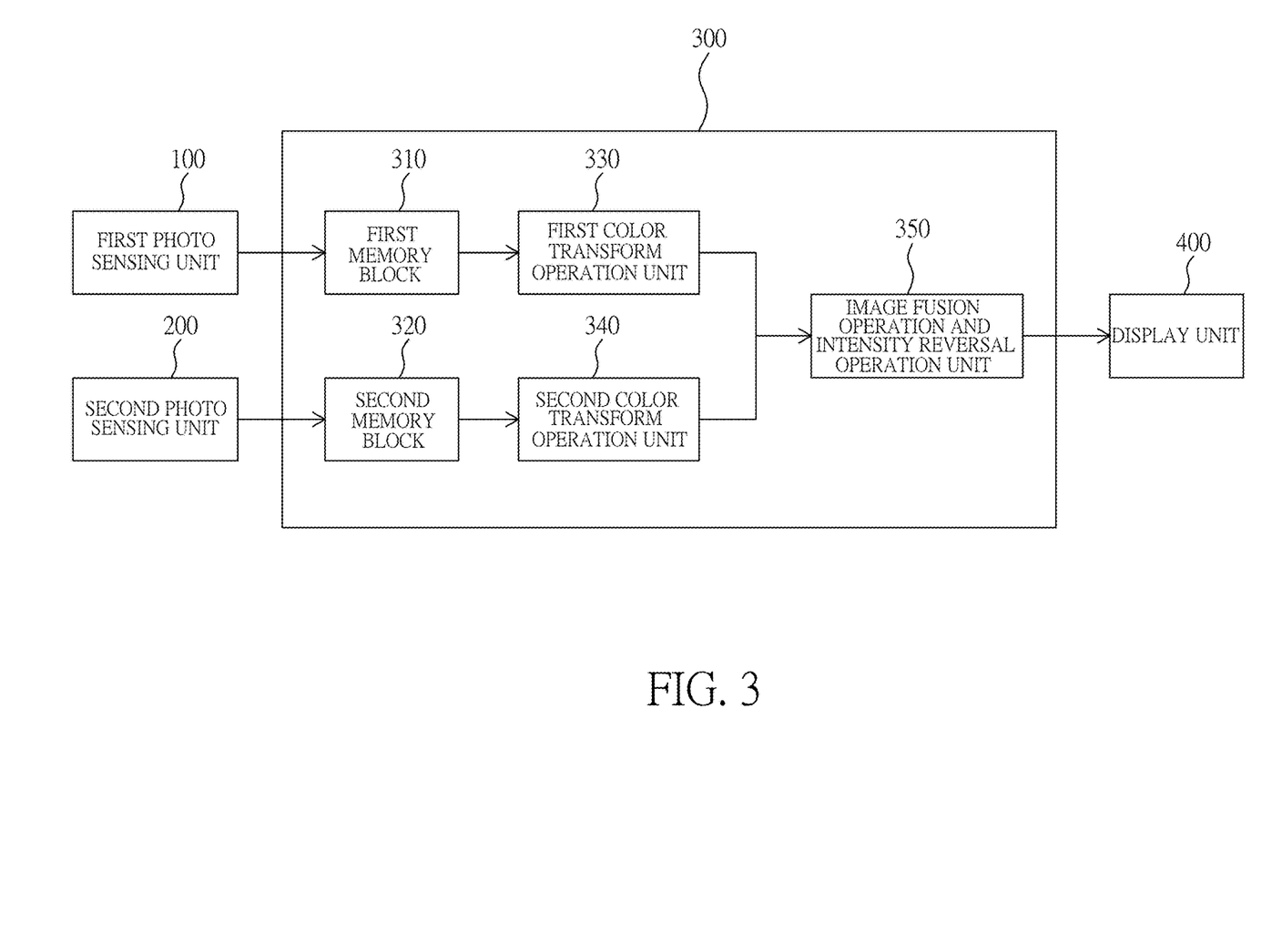
FIG. 3 illustrates a block diagram of an optical system using the pseudo H&E image producing method according to a preferred embodiment of the present invention.

Please refer to FIG. 3, which illustrates a block diagram of an optical system using the pseudo H&E image producing method according to a preferred embodiment of the present invention.

As illustrated in FIG. 3, the optical system includes a first photo sensing unit 100, a second photo sensing unit 200, an information processing apparatus 300, and a display unit 400.

The first photo sensing unit 100 is used for inputting a grayscale interference image or a grayscale reflected image, the grayscale interference image or the grayscale reflected image represents a cytoplasm image, where the grayscale interference image can generated by an optical interference microscopy scheme (not shown in the figure), which uses interference between a light beam and a reflected light beam to generate an image of a pathological sample, and the grayscale reflected image can be generated by a reflectance confocal microscopy scheme (not shown in the figure), which uses a directly reflected light beam to generate an image of a pathological sample.

The second photo sensing unit 200 is used for inputting a grayscale fluorescent image of a pathological sample, where the grayscale fluorescent image represents a nuclei image.

The information processing apparatus 300 is coupled with the first photo sensing unit 100 and the second photo sensing unit 200, and includes a first memory block 310 and a second memory block 320, where the first memory block 310 is used for storing the grayscale interference image or the grayscale reflected image input by the first photo sensing unit 100, and the second memory block 320 is used for storing the grayscale fluorescent image input by the second photo sensing unit 200.

The information processing apparatus 300 further includes a first color transform operation unit 330, a second color transform operation unit 340, and an image fusion operation and intensity reversal operation unit 350.

The first color transform operation unit 330 is coupled with the first memory block 310 for performing a first color transform operation on the grayscale interference image or the grayscale reflected image stored in the first memory block 310 to generate a first RGB image, where the first color transform operation sets both red pixel intensity and blue pixel intensity of the first RGB image to 0, and sets green pixel intensity of the first RGB image equal to the product of pixel grayscale of the grayscale reflected image or the grayscale interference image and a weighting value, the weighting value ranging between 0.5 and 1, so that the first RGB image is a black-background dark green image.

The second color transform operation unit 340 is coupled with the second memory block 320 for performing a second color transform operation on the grayscale fluorescent image stored in the second memory block 320 to generate a second RGB image, where the second color transform operation sets green pixel intensity of the second RGB image to $2^{8m}-1$, m being a positive integer, sets blue pixel intensity of the second RGB image to 0, and sets red pixel intensity of the second RGB image equal to a product of pixel gray scale of the grayscale fluorescent image and a weighting value, the weighting value ranging between 0.5 and 1, so that the second RGB image is a black-background yellow-green image.

Besides, both the first RGB image and the second RGB image use n binary bits to represent red pixel intensity, green pixel intensity, and blue pixel intensity, the n being a positive integer and a multiple of 8. The image fusion operation and intensity reversal operation unit 350 is coupled with the first color transform operation unit 330 and the second color transform operation unit 340 for performing an image fusion operation and an intensity reversal operation on the first RGB image and the second RGB image to generate a pseudo H&E image, which is a white-background pink-and-blue-violet image.

The display unit 400 is coupled with the information processing apparatus 300 to display the pseudo H&E image.

Thanks to the novel designs disclosed above, the present invention possesses the advantages as follows:

1. The pseudo H&E image producing method of the present invention is capable of generating a pseudo H&E image of a pathological sample without the need of performing a physically slicing procedure on the pathological sample, where the pseudo H&E image is a white-background RGB image having excellent color contrast, and is generated by letting an interference image (or a reflected image) and a fluorescent image of the pathological sample undergo a color transform procedure, an image fusion procedure and an intensity reversal procedure.

2. The pseudo H&E image producing method of the present invention is capable of using less fluorescent agent to minimize the damage on a pathological sample caused by the fluorescent agent compared to the prior art method of using multiple fluorescent images.

3. The pseudo H&E image producing method of the present invention, in comparison with the prior art method of using multiple fluorescent images, is capable of using less fluorescent agent to shorten a staining time and thereby speed up the completion of a pseudo H&E image.

4. The pseudo H&E image of the present invention, in comparison with conventional H&E image, is capable of providing more detailed image information of the cytoplasm and nuclei, thereby enhancing the distinguishability between normal tissues and abnormal tissues.

While the invention has been described by way of example and in terms of preferred embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance over the conventional structure and further complies with the patent application requirements and is submitted to the Patent and Trademark Office for review and granting of the commensurate patent rights.

What is claimed is:

1. A pseudo Haemotoxylin and Eosin (H&E) image producing method, including steps of:
   inputting a grayscale interference image or a grayscale reflected image of a pathological sample to a first memory block of an information processing apparatus, the grayscale interference image or the grayscale reflected image having a first image resolution, and inputting a grayscale fluorescence image of the pathological sample to a second memory block of the information processing apparatus, the grayscale fluorescence image having a second image resolution, and the first image resolution being same with or different from the second image resolution;
   using the information processing apparatus to perform a first color transform operation on the grayscale interference image or the grayscale reflected image to generate a first RGB image, and using the information processing apparatus to perform a second color transform operation on the grayscale fluorescence image to generate a second RGB image;
   using the information processing apparatus to perform an image fusion operation and an intensity reversal operation on the first RGB image and the second RGB image to generate a pseudo H&E image; and
   outputting the pseudo H&E image to a display unit;
   wherein the first RGB image is a black-background dark green image; the second RGB image is a black-background yellow-green image; and the pseudo H&E image is a white-background pink-and-blue-violet image.

2. The pseudo H&E image producing method as disclosed in claim 1, wherein the grayscale interference image or the grayscale reflected image represents a cytoplasm image.

3. The pseudo H&E image producing method as disclosed in claim 1, wherein the grayscale fluorescent image represents a nuclei image.

4. The pseudo H&E image producing method as disclosed in claim 1, wherein the grayscale interference image is generated by an optical interference microscopy scheme, which uses interference between a light beam and a reflected light beam to generate an image of the pathological sample.

5. The pseudo H&E image producing method as disclosed in claim 1, wherein the grayscale reflected image is generated by a reflectance confocal microscopy scheme, which uses a directly reflected light beam to generate an image of the pathological sample.

6. The pseudo H&E image producing method as disclosed in claim 1, wherein the first color transform operation sets both red pixel intensity and blue pixel intensity of the first RGB image to 0, and sets green pixel intensity of the first RGB image equal to a product of pixel grayscale of the grayscale reflected image or the grayscale interference image and a weighting value, the weighting value ranging between 0.5 and 1.

7. The pseudo H&E image producing method as disclosed in claim 1, wherein the second color transform operation sets green pixel intensity of the second RGB image to $2^{8m}-1$, m being a positive integer, sets blue pixel intensity of the second RGB image to 0, and sets red pixel intensity of the second RGB image equal to a product of pixel grayscale of the grayscale fluorescent image and a weighting value, the weighting value ranging between 0.5 and 1.

8. The pseudo H&E image producing method as disclosed in claim 1, wherein both the first RGB image and the second RGB image use n binary bits to represent red pixel intensity, green pixel intensity, and blue pixel intensity, the n being a positive integer and a multiple of 8.

9. An optical system comprising:
a first photo sensing unit, a second photo sensing unit, an information processing apparatus, and a display unit, characterized in that:
the first photo sensing unit is used for inputting a grayscale interference image or a grayscale reflected image of a pathological sample to a first memory block of the information processing apparatus, the grayscale interference image or the grayscale reflected image having a first image resolution, and the second photo sensing unit is used for inputting a grayscale fluorescence image of the pathological sample to a second memory block of the information processing apparatus, the grayscale fluorescence image having a second image resolution, and the first image resolution being same with or different from the second image resolution;
the information processing apparatus has a first color transform operation unit coupled with the first memory block for performing a first color transform operation on the grayscale interference image or the grayscale reflected image to generate a first RGB image, and has a second color transform operation unit coupled with the second memory block for performing a second color transform operation on the grayscale fluorescence image to generate a second RGB image;
the information processing apparatus has an image fusion operation and intensity reversal operation unit for performing an image fusion operation and an intensity reversal operation on the first RGB image and the second RGB image to generate a pseudo H&E image; and the information processing apparatus outputs the pseudo H&E image to the display unit;
wherein the first RGB image is a black-background dark green image; the second RGB image is a black-background yellow-green image; and the pseudo H&E image is a white-background pink-and-blue-violet image.

* * * * *